United States Patent [19]
Yannas et al.

[11] Patent Number: 4,947,840
[45] Date of Patent: Aug. 14, 1990

[54] BIODEGRADABLE TEMPLATES FOR THE REGENERATION OF TISSUES

[75] Inventors: Ioannis V. Yannas, Newton; Elaine Lee, Medford; Ariel Ferdman, Cambridge, all of Mass.

[73] Assignee: Massachusetts Institute of Technology, Cambridge, Mass.

[21] Appl. No.: 87,772

[22] Filed: Aug. 21, 1987

[51] Int. Cl.[5] .................... A61L 15/00; A61F 2/10
[52] U.S. Cl. ..................... 128/156; 424/DIG. 13; 623/15; 523/113; 523/114
[58] Field of Search .............. 128/156, 897, 898; 623/15; 600/36; 523/114, 113; 424/DIG. 13

[56] References Cited

U.S. PATENT DOCUMENTS

| 4,060,081 | 11/1977 | Yannas et al. | |
|---|---|---|---|
| 4,252,759 | 2/1981 | Yannas et al. | |
| 4,280,954 | 7/1981 | Yannas et al. | |
| 4,347,841 | 9/1982 | Benyó et al. | 424/DIG. 13 |
| 4,350,629 | 9/1982 | Yannas et al. | |
| 4,361,552 | 11/1982 | Baur, Jr. | 424/105 |
| 4,399,123 | 8/1983 | Oliver et al. | 623/15 |
| 4,418,691 | 12/1983 | Yannas et al. | 128/156 |
| 4,448,718 | 5/1984 | Yannas et al. | |
| 4,458,678 | 7/1984 | Yannas et al. | 623/15 |
| 4,505,266 | 3/1985 | Yannas et al. | 623/11 |
| 4,522,753 | 6/1985 | Yannas et al. | |
| 4,572,906 | 2/1986 | Sparkes et al. | 514/21 |
| 4,642,118 | 2/1987 | Kuroyanagi et al. | 623/15 |
| 4,659,572 | 4/1987 | Murray | 514/774 |
| 4,767,619 | 8/1988 | Murray | 514/774 |
| 4,784,653 | 11/1988 | Bolton et al. | 604/307 |
| 4,841,962 | 6/1989 | Berg et al. | 128/156 |

OTHER PUBLICATIONS

H. F. Fischmeister, Proceedings Int. Symp. RILEM-/UPAC, Prague (1973); Final Report Part II, p. C-439.
*Chemistry and Industry*, p. 905 (1970).
I. V. Yannas, A. V. Tobolsky, *Nature*, 215, pp. 509–510 (1967).
I. V. Yannas et al., *J. Biomed. Mat. Res.*, 14:65–81, 107–131, 511–528 (1980).
E. Lee, Masters Thesis, Massachusetts Institute of Technology, 1986.

*Primary Examiner*—C. Fred Rosenbaum
*Assistant Examiner*—Sharon Rose
*Attorney, Agent, or Firm*—Hamilton, Brook, Smith & Reynolds

[57] ABSTRACT

This invention relates to porous, biodegradable materials in which the pore size, biodegradation rate, and pore volume fraction are controlled and within values at which skin contraction rates around an implant-containing wound are delayed or slowed.

12 Claims, 2 Drawing Sheets

BIODEGRADABLE TEMPLATES FOR THE REGENERATION OF TISSUES

Government Support

The invention described herein was supported in whole or in part by a grant from the National Institutes of Health.

Background of the Invention

Currently there is a variety of general approaches to the treatment of loss of tissue which results either from trauma or from elective surgery. One approach, transplantation, suffers from the fact that the host typically rejects the tissue of the donor. A second, autografting, bypasses the problem of immunological rejection but suffers from two disadvantages: tissue for autografting must be removed from the patient thereby subjecting the latter to additional serious surgery and, additionally, when the trauma is massive there is not sufficient intact tissue to be harvested for the autografting. A third approach attempts to synthesize tissues by culturing in vitro cells of the patient and, suffers from the fact that the culture process is lengthy as well as from the fact that techniques are not still generally available for culturing tissues (the epidermis seems to be the only exception). A fourth approach to tissue repair consists in the fabrication of devices using metals (hip prosthesis), ceramics (bone prosthesis) or polymers (artificial heart). This approach suffers from the acute incompatibility, (mechanical, physicochemical and biological), between implant and host tissue which typically leads to device failure within a period of time which is much less that the patient's lifetime.

A fifth approach to treatment of tissue loss consists in treating the wounded tissue with a biodegradable polymeric material which, acting as a scaffold, induces the wound to synthesize new tissue.

An example of such a biodegradable polymeric material is a material formed from crosslinked collagen molecules that are covalently bonded to glycosaminoglycan molecules. These polymer materials have been described in the scientific literature and the patent literature. See, for example, U.S. Pat. No. 4,505,266 (Mar. 19, 1985); U.S. Pat. No. 4,448,718 (May 15, 1984); U.S. Pat. No. 4,418,691 (Dec. 6, 1983); U.S. Pat. No. 4,458,678 (July 10, 1984); U.S. Pat. No. 4,350,629 (Sept. 21, 1982); U.S. Pat. No. 4,522,753 (June 11, 1985); U.S. Pat. No. 4,280,954 (July 28, 1981); U.S. Pat. No. 4,252,759 (Feb. 24, 1981); and U.S. Pat. No. 4,060,081 (Nov. 29, 1977) the teachings of which are incorporated herein by reference.

A need has long existed, however, for an artificial skin implant in which the rate of skin contraction around a wound is lowered, thereby reducing the amount of scar tissue formed.

Summary of the Invention

The present invention is based upon the discovery that the contraction rate of full thickness skin wounds around an artificial skin implant may be significantly slowed if the biodegradation rate and average pore size of the implant are maintained within selected parameters. Specifically, this invention pertains to a polymeric, biodegradable material in which both the biodegradation rate and the pore size are selected and maintained to provide efficacious use of the material as a scaffold for wound repair. One specific example of a material is a crosslinked collagen-glycosaminoglycan in which crosslinking has been carried out by contacting the composite with an aqueous glutaraldehyde solution for a sufficient time. This yields a degree of crosslinking which is inversely proportional to the rate of biodegradation of the material. Additionally, the material is produced in a manner in which the average pore size is between approximately 9 $\mu$m and approximately 630 $\mu$m.

Detailed Description of the Invention

Figure 1:
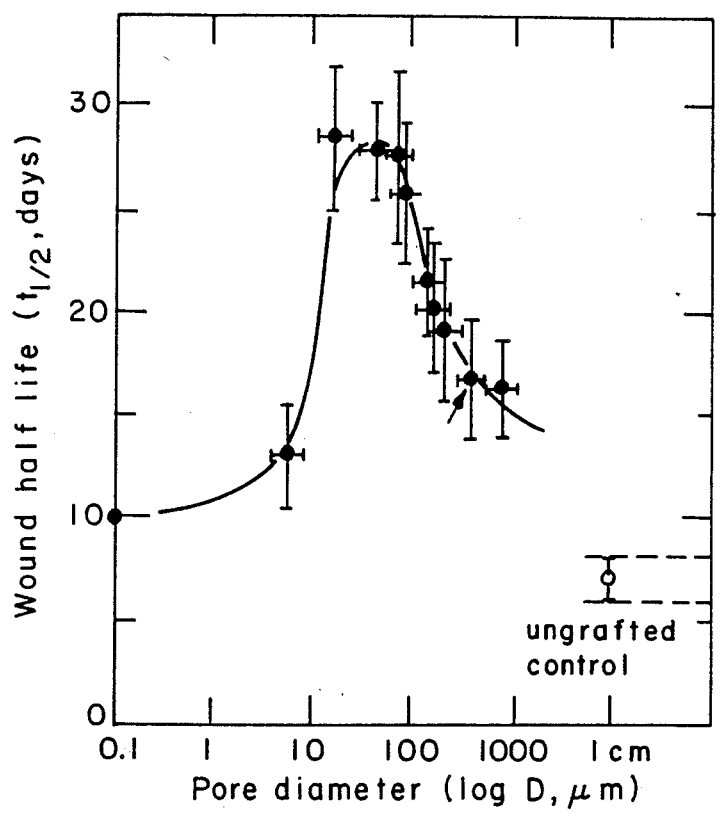
FIG. 1 is a plot correlating the effects of average pore size of a crosslinked collagenglycosaminoglycan skin graft implanted at the wound site of guinea pigs on the inverse rate of wound closure by contraction.

The key to a successful artificial skin implant lies in certain critical parameters of the implant material. These parameters are the biodegradation rate of the material, the mean pore size of the material, and the pore volume fraction of the material.

Artificial skin implants may be produced from a variety of collagen-based materials in which the collagen, either alone or in combination with a glycosaminoglycan, a glycoprotein, a structural protein or a growth factor is crosslinked. Suitable glyoproteins include fibronectin, laminin and chondronectin. A suitable structural protein is elastin. Growth factors may be epidermal growth factor, platelet derived growth factor, tissue angiogenesis factor, nerve growth factor and bone growth factor. In addition, certain collagen-free materials can also be used, provided they have the proper combination of critical parameters discussed above. For example, synthetic materials such as polylactides or polyglycolic acids, can be used as skin implants.

Methods of preparing polyactides are well documented in the patent literature. The following U.S. Patent Nos., the teachings of which are hereby incorporated by reference, describe in detail suitable polylactides, their properties and their preparation: Dorough, U.S. Pat. No. 1,995,970; Schneider, U.S. Pat. No. 2,703,316; Salzberg, U.S. Pat. No.2,758,987, Zeile, U.S. Pat. No. 2,951,828; Higging, U.S. Pat. Nos. 2676,945; 2,683,136; Trehu, U.S. Pat. No. 3,531,561; British Patent specification Nos. 755,447; 779,291; 825,335, 901,037; 932,382; 1,048,088; 1,123,445; West German Patent Nos. 946,664; 975,191; 1,112,293; 1,152,258; 1,153,902; East German Patent Nos. 14,548; French Patent Nos. 1,425,333; 1,478,694; 1,512,182; Netherlands Patent Nos. 99,836; 6,605,197; 6,605,292; Japanese Patent Nos. 17,675 (1966); 7,796 (1967); 2,948 (1968); 15,789 (1969).

Polyglycolic acids and their properties are described in more detail in the following article, the teachings of which are hereby incorporated by reference: "Cyanamid Research Develops World's First Synthetic Absorbably Suture", Chemistry and Industry, July 11, 1970, Page 905.

A preferred artificial skin implant comprises a composite formed from collagen molecules that are crosslinked and covalently bonded with glycosaminoglycan (GAG). Examples of specific glycosaminoglycans are chondroitin 6-sulfate, chondroitin 4-sulfate, heparan, heparan sulfate, keratan sulfate, dermatan sulfate, chitin or chitosan. Such a composite can be made by forming an uncrosslinked material comprising a reaction product of collagen and a glycosaminoglycan and contacting the reaction product with an aqueous glutaraldehyde solution for a period in excess of one hour. The resulting crosslinked collagen-glycosaminoglycan composite has a rate of biodegradation which is low enough to enable the composite to be a suitable scaffold for wound repair.

The biodegradation rate of the crosslinked implant material is inversely related to the degree of crosslinking in the material. It has been found that crosslinked composites should have an average molecular weight between crosslinks, ($M_c$), of between about 800 and about 60,000 daltons. Materials with $M_c$ values below about 800 and above about 60,000 suffer significant losses in their mechanical properties. Composites with an $M_c$ of between 10,000 and about 40,000 tend to have the best balance between physical and therapeutic properties. Thus, this is the preferred range of crosslinking for products requiring such a balance of properties.

Covalent crosslinking can be achieved by many specific techniques with the general catagories being chemical, radiation and dehydrothermal methods. An advantage to most crosslinking methods contemplated, including glutaraldehyde crosslinking and dehydrothermal crosslinking, is that they also serve to remove bacterial growths from the materials. Thus, the composites become sterilized while simultaneously being crosslinked.

One suitable method for covalently crosslinking the collagen-GAG composites is known as aldehyde crosslinking. In this process, the materials are contacted with aqueous solutions of aldehyde, which serve to crosslink the materials. Suitable materials include formaldehyde, glutaraldehyde and glyoxal. Glutaraldehyde is preferred because it yields the desired level of crosslink density more rapidly than other aldehydes and is also capable of increasing the crosslink density to a relatively high level. It has been noted that immersing the composites in aldehyde solutions causes partial removal of the polysaccharide component by dissolution thereby lessening the amount of polysaccharide in the final product. Unreacted aldehydes should be removed from the collagen-GAG material by exhaustive rinsing with water since residual aldehydes are quite toxic.

Other suitable chemical crosslinking techniques include carbodiimide coupling, azide coupling and diisocyanate crosslinking.

Another crosslinking method is referred to herein as a dehydrothermal process. In dehydrothermal crosslinking, no external crosslinking agents need to be added to the composite. Rather, the composite is dehydrated to a moisture content of less than about 1%. The actual amount of water which must be removed will vary with many factors, but, in general, sufficient water to achieve the desired crosslinking density must be removed. Thus, a collagen-GAG product can be subjected to elevated temperatures and/or vacuum conditions until the moisture content is reduced to extremely low levels and the desired crosslinking density is achieved. In the absence of a vacuum, temperatures about 80° C., and perferably above about 90° C. can be used. On the other hand, if the process is to be performed at approximately 23° C., a vacuum of at least $10^{-5}$ mm Hg, and preferably below about $10^{-6}$ mm Hg is suitable. In the preferred embodiment of this process, elevated temperatures and vacuum can be used in combination to expedite crosslinking. With a vacuum of at least about $10^{-5}$ mmHg, it is preferred to use a temperature of at least about 35° C. In general, the materials are subjected to the elevated temperatures and vacuum conditions until the desired degree of crosslinking density is achieved. The higher the temperature, the lower is the vacuum required to arrive at a given crosslink density; and vice versa. This dehydrothermal crosslinking process overcomes certain disadvantages of the aldehyde crosslinking method and produces composites having relatively large amounts of GAG strongly bound to the collagen chain.

The exact mechanism operating in the dehydrothermal crosslinking process in not known. However, it is believed to be either an amide condensation involving $\epsilon$-amino groups from collagen and carboxyl groups from the GAG component, or esterification involving carboxyl groups from the GAG component and hydroxyl groups from the collagen, or esterification involving hydroxyl groups from the GAG component and carboxyl groups from the collagen. It is possible all three mechanisms are involved to some extent. For a more detailed description of dehydrothermal crosslinking, see Yannas, I.V. and Tobolsky, A.V., "Crosslinking of Gelatin by Dehydration", Nature, vol. 215, # 5100, pages 509-510, July 29, 1967, the teachings of which are hereby incorporated by reference.

The degree of crosslink density is an important parameter of this invention since it is a direct, controlling factor in the degradation rate of the material. Generally, the greater the crosslink density, the lower the degradation rate, and vice versa. Thus, by controlling the degree of crosslinking, it is possible to produce composites which exhibit a degradation rate within a range determined to be clinically desirable. The maximum degradation rate has been determined to be about 140 enzyme units (e.u.) as measured in a test described below. This upper limit in degradation rate is critical since it has been determined that implants with degradation rates higher than about 140 e.u. fail to significantly delay wound contraction. In the preferred embodiment of this invention, the biodegradation rate is below about 120 e.u.

The effectiveness of polymeric scaffolds in slowing or delaying contraction around a wound is further increased by controlling the average pore size of the implant within an upper and a lower limit. To effectively slow or delay wound contraction, and thus serve the purpose of this invention, the implant must contain pores whose average size is within the range of about 9 $\mu$m to about 630 $\mu$m. In the preferred embodiment of this invention, the average pore size is within the range of about 9 $\mu$m to about 630 $\mu$m. Both the 9 $\mu$m and the 630 $\mu$m limits are critical as it has been found that implants with average pore sizes smaller than about 9 $\mu$m or greater than about 630 $\mu$m fail to significantly delay wound contraction.

Polymeric materials which are fabricated by methods which yield a low enough biodegradation rate and pore size within the desired upper and lower limits have been found to effectively delay or arrest skin wound contraction and induce synthesis of new functional tissue. Materials which do not come within the proper parameters do not delay or arrest skin wound contraction and tend to induce synthesis of undesirable scar tissue.

Another determining factor in the effectiveness of artificial skin implants is the pore volume fraction of the implant material. This value is defined as the percentage of the total volume of the material which is occupied by pore space. A more detailed definition is given in Fischmeister, H.F., Proceedings Int. Symp. RILEM/IUPAC, Prague, Sept. 18–21, 1973, Final Report Part II, p. C-439 the teachings of which are incorporated herein by reference. A high pore volume fraction has been found to be clinically desirable, with implants having pore volume fractions above about 80% being preferred.

Exemplification

Bovine hide collagen, chondroitin-6-sulfate (C-6-S, 0.11% w/v), acetic acid (0.05M, pH 3), deionized water, medical-grade 7-mil silicone sheeting and silicone medical adhesive, isopropanol (70%), and phosphate-buffered saline, were used in the manufacture and processing of the collagen-GAG membranes. The crosslinking agent was glutaraldehyde (reagent grade, Aldrich Chem. Col, Milwaukee, WI) diluted in 0.05M acetic acid.

Membranes for use as controls were prepared according to the Stage 1 artificial skin protocol developed by Yannas et al. "Design of an Artificial Skin", J. Biomed. Mat. Res., 14:65–81, 107–131, 511–528 (1980). The specific procedure employed is now set forth and unless otherwise noted, the procedures were done at room temperature.

1. Blend 1.65 g of milled collagen with 600 ml of 0.05 M acetic acid (pH3) for 1 hour at 4° C.
2. Dropwise add 120 ml of C-6-S solution to the blending collagen dispersion over 15 minutes at 4° C. (8% w/w of C-6-S is added to the collagen, but no assay was done to measure the amount retained after the last step.)
3. Blend an additional 15 minutes at 4° C.
4. Centrifuge at 1500g in a 4° C. centrifuge for 105 minutes.
5. Decant 420 ml of supernatant.
6. Reblend slurry for 15 minutes at 4° C.
7. Pour into stainless-steel trays (2 ml per square inch of tray surface); freeze 1 hour at −40° C.
8. Allow to lyophilize (freeze-dry) 24 hours at 0° C. and 100 mtorr.
9. Place foam in vacuum oven at 105° C., 50 mtorr for 24 hours (dehydrothermal treatment).
10. Seal and store in desiccator until ready for next step.
11. Apply silicone layer.
12. Rehydrate in 0.05 M acetic acid (pH 3) for 24 hours.
13. Crosslink in 0.25% glutaraldehyde (pH 3) for 24 hours.
14. Rinse thoroughly with deionized water.
15. Immerse in deionized water for 24 hours.
16. Store in 70% isopropanol at 4° C.

Steps 10 through 16 were done with sterile technique if the artificial skin was to be used for animal experimentation. Step 11 was omitted for membranes that were not to be used in vivo. For membranes to be used as grafts and also to be tested in vitro, the silicone was applied to only about a third of the membrane. Membranes containing different amounts of GAG were prepared by using different concentrations of C-6-S for Step 2 discussed above. For membranes containing no GAG (i.e., crosslinked collagen) Step 4 was changed to centrifugation at 17,000g at 4.C for 2 hours. This was necessary due to the reduction in density of the collagen dispersion caused by the absence of GAG.

One method of varying crosslink density was to vary the length of crosslinking time in 0.25% glutaraldehyde (Step 13). Another way was to multiply the concentration of glutaraldehyde ten times to 2.5% while keeping the crosslinking time at 24 hours.

A third, completely different method of inducing very high crosslink densities was crosslinking with glutaraldehyde vapor at controlled temperature and relative humidity.

To determine the approximate average pore size in the collagen-GAG membranes, samples were embedded in methacrylate, sectioned to 5 $\mu$m thickness, mounted on a glass slide, and stained with 1% toluidine blue. The slides were examined under a light microscope at 125x magnification. The diameter of the field of vision through the microscope was 0.138 inch. The number of pores across the field was counted at various locations on the slide and different orientations. At least 6 such countings were done for each membrane. Pore size was calculated at the field size divided by the number of pores across the field. The mean and standard deviation of the 6 or more numbers representing pore size were then calculated.

The molecular weight between crosslinks in the membranes, $M_c$, was determined by the $M_c$ test. In this test, strips of artificial skin material were gelatinized in 80° C. normal saline and the equilibrium tensile stress was studied as a function of equilibrium strain. Gelatinization destroys the triple helical structure of collagen. The gelatinized material is modelled as a swollen, ideal rubber. The $M_c$ can be calculated from the equilibrium stress-strain relation of the material. For each type of membrane, at least 4 strips were tested. The mean and standard deviation of the $M_c$ values of these strips were calculated. Molecular weight between crosslinks is an inverse measure of crosslink density. A more detailed discussion of the $M_c$ test may be found in U.S. Pat. No. 4,060,081, the teachings of which have previously been incorporated by reference.

The biodegradation rate of the various membranes was characterized using a modified collagenase assay from the Sigma Chemical Company (1977). In preparation for the assay, the membranes were first refreeze-dried (Steps 7 and 8 discussed previously).

In the assay, the material to be tested was incubated for 5 hours with collagenase from Clostridium bistolyticum (GIBCO, Grand Island, N.Y.). This bacterial collagenase hydrolyzes proteins containing proline. The amino groups liberated were measured as equivalents of L-leucine using a colorimetric ninhydrin method. The darker the final solution, the higher the concentration of free amino groups, and thus the faster the degradation of the material.

Bovine Achilles tendon collagen (Type I, insoluble) from the Sigma Chemical Company was used as a standard. It gives a known activity of 202 enzyme units. By definition (Sigma 1977), one enzyme unit "will liberate Amino Acids from Collagen equivalent in Ninhydrin color to 1.0 Mole of L-Leucine in 5 hours at pH 7.4 at 37° C."

The units measured using this assay are referred to as "enzyme units". Enzyme units are a measure of the in vitro degradation rate of the material being tested. The higher the number of enzyme units, the greater the degradation rate.

Unprocessed 20-mesh milled bovine collagen (the major raw material in the manufacture artificial skin) was used as a control. When the enzyme units of a day's assay were calculated and normalized to the Sigma standard of 202, the bovine collagen was expected to yield enzyme units in the range of 178±15.

The following summarizes the steps in the collagenase assay.

1. For each collagen type weigh out 0.025 g of collagen into each of 4 test tubes; one tube is the spectrophotometric blank.
2. Incubate each test sample in 5 ml of a pH 7.4 buffer with 0.10 ml of a buffered solution of 0.08% w/v collagenase (0.10 ml deionized water in each blank) for 5 hr at 37° C.; stir continuously by using a magnetic flea in each tube.
3. Filter the contents of each tube to eliminate turbidity that may interfere with the spectrophotometric measurements; save 0.20 ml of each filtrate.
4. Add 2 ml of a pH 5.5 ninhydrin-and-hydrindantin solution to stop the enzymatic reaction and to induce color.
5. Place the tubes in a boiling water bath for 20 min.
6. Mix in 10 ml of 50% propanol, or 5 ml for highly crosslinked materials; let stand 15 min at room temperature to develop and fix color.
7. Record transmittance at 600 nm.

Steps 4 through 7 were also done on a calibration tube containing 0.20 ml of 0.002M L-leucine and on a corresponding blank containing 0.20 ml of deionized water.

The enzyme units of each test (3 test tubes per collagen type) were calculated from the transmittances and by comparison to the calibration test indicating the transmittance of a known amount of L-Leucine. The mean standard deviation of each set of 3 results was determined. Finally, these numbers were multiplied by the factor which normalized the mean enzyme units for Sigma collagen to 202.

A bacterial collagenase is used in the assay, while the collagenase in a guinea pig or human is mammalian. This means that the enzyme units do not indicate the actual degradation rate of a graft in a wound. Rather, the assay is an in vitro tool used to determine quantitatively the relative biodegradabilities of graft materials.

In vivo response to various collagen membranes was studied by grafting onto guinea pigs. White female Hartley guinea pigs (Elm Hill Breeding Labs, Chelmsford, MA) were allowed to stabilize in the MIT Animal Facility for at least one week after arrival at the facility. Each guinea pig weighed between 430 and 810 g at surgery.

Each animal was initially anesthetized by inhalation of 2% Halothane in 0.5 liters/min oxygen and 2 liters/min nitrous oxide. During the course of surgery, the Halothane level was gradually reduced. Approximately 2 minutes before the completion of surgery, the animal was taken off anesthesia and given 2 liters/min pure oxygen for about 5 minutes.

After the outline of the wound was made with a scalpel on the back of the animal, the dimensions of the outline were measured. Care was taken to avoid any stretching or buckling of the skin at the wound site during measurement. The nominal wound dimensions were 1.5 cm by 3.0 cm. The "original wound area" was calculated as the product of the mean of the long dimensions and the mean of the short dimensions.

Every 3 or 4 days, the area of the wound was determined. Five dimensions were measured: the length at both sides of the wound, the width at both ends, and the width at the middle. Local effects of any sutures pulling the intact skin over the wound were avoided by taking measurements slightly away from such irregularities. In, cases where the wound was far from rectangular, a judgment was made to decide where to make measurements. The intent was to have the product of the means of the length and width measurements most accurately represent the actual area of the wound. Errors in area measurement from human judgment and from stretching or gathering of skin are estimated to be 15%.

The area measured was initially the pink area under the graft. When a slightly darker band appeared around the pink area during the course of healing, this band was also included in the area measured. The pink area eventually disappeared as the wound edges came together, and the darker area remained as a scar. Measurements taken in this way were designated "pink-and-dark area". The forked ends of the scar were not included in the area measurements.

It is believed that the darker area is vascularized collagen-GAG covered by epidermal ingrowth from the wound edges. This area is surrounded by healthy dermis containing hair follicles and hair. The hair closest to the wound edge is often too small to see. Thus, the area within the visible hairline( designated the "hairline area") is an upper bound for the pink-and-dark area.

The main parameter to gauge graft efficacy is a determination of the day at which, following surgery, the wound has reached approximately half of its original area. This parameter is defined as $D_{50}$. $D_{50}$ roughly indicates the rate of wound closure by contraction. The wound area closes by two mechanisms: epidermal ingrowth from the wound edges (epithelialization), and drawing together of the wound edges (contraction). Epithelialization occurs at a fairly constant rate, whereas contraction is a function of graft material. The greater the $D_{50}$ the slower the contraction, and therefore the better the graft.

Results

Effects of pore size are summarized in FIG. 1. Materials with different pore sizes were prepared in different ways, but all were processed identically after the freezing step (after Step 8 described previously). All were crosslinked in 0.25% glutaraldehyde in 0.05 M acetic acid for 24 hours at room temperature.

Control of the mean pore size was a very effective procedure for delaying wound contraction. Using an arbitrary cut-off level of $D_{50}=15$ days, FIG. 1 may be used to estimate a lower mean pore size limit of about 9 $\mu$m and an upper mean pore size limit of about 630 $\mu$m. In the preferred embodiment of this invention, a maximum increase of $D_{50}=27$ days occurred when the mean pore size varied between the narrower limits of about 20 $\mu$m and about 125 $\mu$m.

Thus, it is important to consider both upper and lower limits of pore diameter when comparing the wound-healing efficacy of different graft materials.

Pores are formed by ice nucleation during the freezing step. Pore size is temperature-dependent. At very low temperatures, the collagen-GAG slurry freezes very quickly, locking tiny ice crystals into place soon after nucleation. At higher temperatures (but still below freezing temperatures), the ice crystals have time to grow and fuse together before the slurry is frozen solid, resulting in larger pores.

It has been shown that the specific surface of the material being tested does not affect the results of the collagenase assay. This implies that differences in pore size do not affect assay values because of any differences in surface area. This is expected since the enzyme attacks the protein molecules on a scale much smaller than the size of the pores formed in the artificial skin during the freeze-drying step.

Figure 2:
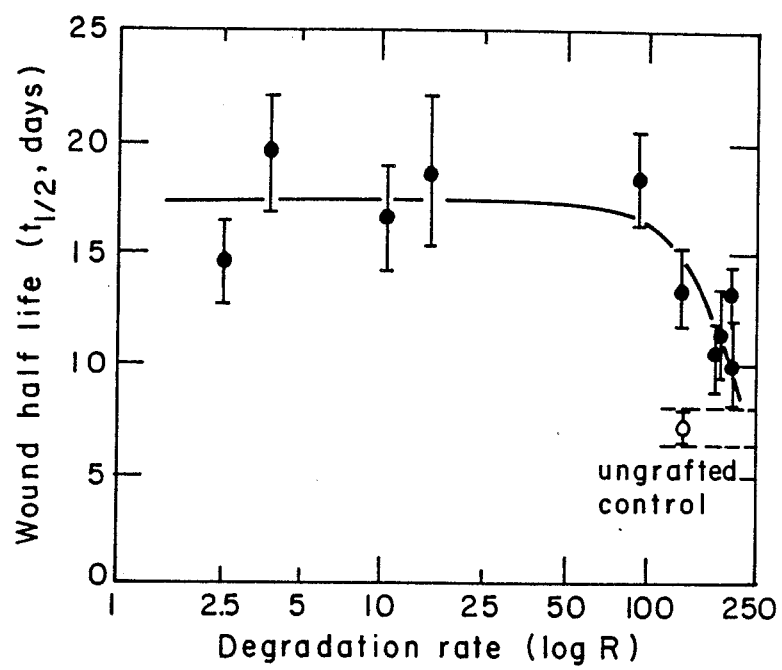
FIG. 2 correlates the dependence of the rate of wound closure on degradation rate for collagen-GAG grafts which were crosslinked in aqueous glutaraldehyde.

FIG. 2 shows $D_{50}$ as a function of enzyme units for the grafts which were crosslinked with aqueous glutaraldehydes. To examine the lower end of the range more easily, the degradation rate is plotted on a logarithmic scale. The x-axis standard deviations have been omitted.

The ten fold difference in degradation rate between materials at 20 enzyme units ($D_{50}=17$ days) and those at 200 units ($D_{50}=11$ days) clearly resulted in difference in wound contraction. Slower graft degradation slowed contraction.

It has further been found that $D_{50}$ varies as a function of crosslink density for aqueously crosslinked grafts.

Equivalents

Those skilled in the art will recognize, or be able to ascertain, using no more than routine experimentation, many equivalents to the specific embodiment of the invention described herein. For example, the glutaraldehyde crosslinking process should not be limited to methods using aqueous glutaraldehyde, as gaseous forms may be used as well. Also, the materials described herein should not be limited to skin implants, but may be used for other organs such as nerve fibers, peridontal tissues and blood vessels. This disclosure is intended to extend to all biodegradable implant materials of the type described in which the degradation rate, pore size and pore volume fraction are within the limits described to yield effective results. Such equivalents are intended to be encompassed in the following claims.

We claim:

1. A method of delaying or arresting contraction of skin bordering a wound site and promoting tissue regeneration, comprising applying a biodegradable material with a pore size of between about 9 $\mu$m and 630 $\mu$m, a pore volume fraction of greater than about 80%, and a biodegradation rate sufficient to significantly delay or arrest the rate of wound contraction such that the time it takes a wound to contract to one-half of its original area is greater than approximately 15 days.

2. A method as in claim 1 wherein the biodegradable material comprises collagen molecules.

3. A method as in claim 1 wherein the biodegradable material comprises collagen molecules that are crosslinked and covalently bonded with a second material selected from the group consisting of glycosaminoglycans, glycoproteins, structural proteins and growth factors.

4. A method as in claim 3 wherein the second material is a glycosaminoglycan selected from the group consisting of chondroitin 6-sulfate, chondroitin 4-sulfate, heparin, heparan sulfate, keratan sulfate, dermatan sulfate, chitin and chitosan.

5. A method as in claim 3 wherein the second material is a glycoprotein selected from the group consisting of fibronectin, laminin and chondronectin.

6. A method as in claim 3 wherein the second material is a structural protein comprising elastin.

7. A method as in claim 3 wherein the second material is a growth factor selected from the group consisting of epidermal growth factor, platelet derived growth factor, tissue angiogenesis growth factor and bone growth factor.

8. A method as in claim 3 wherein the biodegradable material is crosslinked by contacting it with an aqueous aldehyde.

9. A method as in claim 8 wherein the aldehyde is glutaraldehyde.

10. A method as in claim 1 wherein the biodegradable material contains pores with an average size ranging from about 20 $\mu$m to about 125 $\mu$m.

11. A method as in claim 1 wherein the biodegradable material has a degradation rate in an in vitro collagenase assay of below about 140 enzyme units.

12. A method as in claim 11 wherein the biodegradable material has a degradation rate in an in vitro collagenase-assay of below about 120 enzyme units.

* * * * *

UNITED STATES PATENT AND TRADEMARK OFFICE

CERTIFICATE EXTENDING PATENT TERM
UNDER 35 U.S.C. § 156

PATENT NO.      :   4,947,840

ISSUED          :   August 14, 1990

INVENTOR(S)     :   Ioannis V. Yannas et al.

PATENT OWNER    :   Massachusetts Institute of Technology

PRODUCT         :   INTEGRA® Artificial Skin

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 923 days from August 21, 2007, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 23rd day of October 1998.

Bruce A. Lehman
Assistant Secretary of Commerce and
  Commissioner of Patents and Trademarks